United States Patent [19]
McGill et al.

[11] Patent Number: 5,880,552
[45] Date of Patent: Mar. 9, 1999

[54] DIAMOND OR DIAMOND LIKE CARBON COATED CHEMICAL SENSORS AND A METHOD OF MAKING SAME

[75] Inventors: Robert Andrew McGill, Woodbridge; Paul Christopher Dorsey, Alexandria, both of Va.; Douglas Brian Chrisey, Bowie, Md.

[73] Assignee: The United States of America as represented by the Secretary of the Navy, Washington, D.C.

[21] Appl. No.: 863,593

[22] Filed: May 27, 1997

[51] Int. Cl.$^6$ .......................... G01N 29/18; H01L 41/08
[52] U.S. Cl. .......................... 310/313 R; 310/328
[58] Field of Search .................. 310/313 R, 328

[56] References Cited

U.S. PATENT DOCUMENTS

| | | | |
|---|---|---|---|
| 4,537,791 | 8/1985 | Tarjan | 427/2 |
| 4,952,832 | 8/1990 | Imai et al. | 310/313 A |
| 5,012,668 | 5/1991 | Haworth | 73/240.06 |
| 5,076,094 | 12/1991 | Frye et al. | 73/19.03 |
| 5,091,051 | 2/1992 | Greer | 156/643 |
| 5,151,110 | 9/1992 | Bein et al. | 55/75 |
| 5,221,870 | 6/1993 | Nakahata et al. | 310/313 A |
| 5,235,235 | 8/1993 | Martin et al. | 310/313 D |
| 5,243,539 | 9/1993 | Holt et al. | 364/500 |
| 5,294,858 | 3/1994 | Nakahata et al. | 310/313 A |
| 5,329,208 | 7/1994 | Imai et al. | 310/313 R |
| 5,418,058 | 5/1995 | Li et al. | 428/327 |
| 5,426,340 | 6/1995 | Hikagi et al. | 310/313 R |
| 5,440,189 | 8/1995 | Nakahata et al. | 310/313 R |
| 5,446,329 | 8/1995 | Nakahata et al. | 310/313 A |
| 5,571,401 | 11/1996 | Lewis et al. | 205/406 |
| 5,776,246 | 7/1998 | Tanabe et al. | 117/89 |
| 5,814,525 | 9/1998 | Renschler et al. | 436/524 |

*Primary Examiner*—Thomas M. Dougherty
*Attorney, Agent, or Firm*—George A. Kap; Thomas E. McDonnell

[57] ABSTRACT

A water vapor insensitive and corrosion resistant chemical or biochemical sensor device, including a transducer, coated with a protective coating of diamond or a diamond-like carbon, preferably by a pulsed laser deposition technique. The surface of the protective coating is coated with a chemoselective or bioselective absorption material or film.

11 Claims, 3 Drawing Sheets

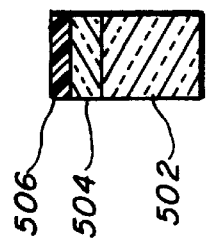
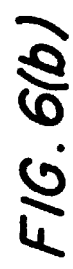
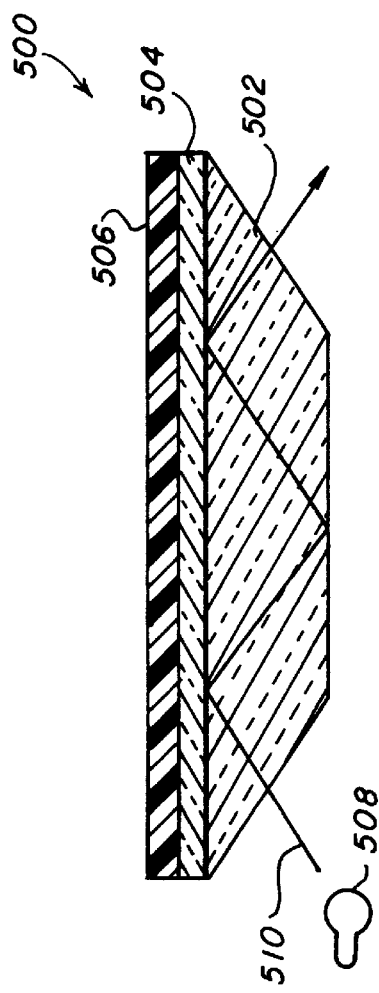
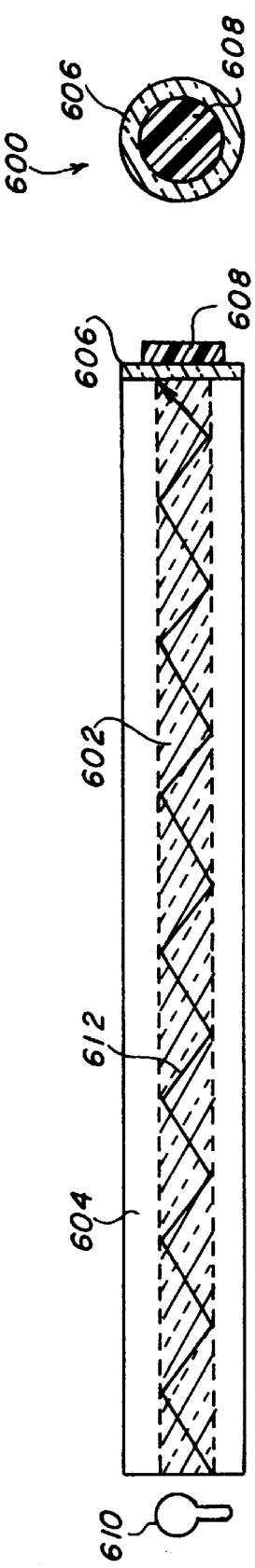

DIAMOND OR DIAMOND LIKE CARBON COATED CHEMICAL SENSORS AND A METHOD OF MAKING SAME

FIELD OF THE INVENTION

The present invention relates to improved acoustic and optical wave chemical sensor devices and to a method of forming the devices. In particular, the invention relates to coating the wave chemical sensors with a protective coating of diamond or a diamond-like carbon (DLC) to improve device performance, durability and corrosion resistance when the device is in contact with a corrosive or a moist atmosphere or environment.

BACKGROUND OF THE INVENTION

Acoustic and optical wave chemical sensors are relatively new forms of chemical sensors which are based on transducers that monitor physical changes in a coating material or the surface of the transducer as material is sorbed either onto the surface of a material or into the bulk material. In acoustic wave device, when the wave is confined to the surface of the device, the sensor is characterized as a surface acoustic wave sensor and when the bulk material is vibrating, the is sensor characterized as a bulk acoustic wave sensor.

Acoustic wave sensors have been described by J. Grate et al in *Analytical Chemistry*, 1993, Vol. 65, No. 22, pp. 987A–995A, and in *Analytical Chemistry*, 1993, Vol. 65, No. 21, pp. 940A–948A, herein incorporated by reference. In the systems, the detector vibrates at a predetermined frequency and the frequency changes as material is sorbed. Acoustic wave chemical sensors have been shown to work in a variety of sensing environments and applications including detecting gases, vapors and selected species within gases and liquids. An example of an acoustic wave sensor is a surface acoustic wave (SAW) sensor.

A two-port SAW sensor includes an input transducer for generating an acoustic wave, an interaction or active region in which the propagating wave interacts with the environment, and an output transducer for detecting the wave. The acoustic wave characteristics can be altered by changes in material on or near the device surface. The cumulative effects of such an interaction over the propagation path of the acoustic wave result in changes in wave velocity, wave amplitude, wave frequency and phase delay at the output transducer. In the simplest cases, acoustic wave devices function as highly sensitive detectors of changes in surface mass, responding primarily to accumulated mass per unit area. Specific sensors are made by coating a film capable of sorbing a particular species or class of species from the environment to the interaction region of the device.

A number of prior art patents and articles describe acoustic chemical sensor devices. For example, U.S. Pat. No. 5,235,235, the subject matter of which is incorporated herein by reference, describes a multi-frequency acoustic wave sensor device for chemical sensing in both gas and liquid phases. The sensor detects changes in the surface wave at several different frequencies to obtain the sensor response.

J. W. Grate and R. A. McGill in *Analytical Chemistry*, 1995, Vol. 67, No. 21, pp. 4015 to 4019, the subject matter of which is incorporated herein by reference, describe making chemical acoustic wave detectors by applying a thin polymer film to a surface acoustic wave device. The author also describe how certain polymers fail to wet the surface of the SAW and how certain polymers, once coated on the surface as a film, will dewet. The dewetting process results in separation of the polymer from the surface and the formation of globular polymer structures on the SAW surface.

Polymer coated SAW devices have been used for the detection and monitoring of gases and vapors in gaseous atmospheres. R. Andrew McGill et al. in *Surface and Interfacial Properties of Surface Acoustic Wave Gas Sensors*, ACS Symposium Series 561, Chap. 24, pp. 280–294, the subject matter of which is incorporated herein by reference, describe some of the problems of a conventional surface acoustic wave gas sensor herein the SAW device has a polymer film coating.

A major problem of conventional chemical sensor devices is the interfacial sorption of water vapor at the device substrate-coating interface. This sorption of water vapor is a particular problem with quartz, presently the most popular piezoelectric material, because the quartz surface has silanol and silyl ether moieties which interact strongly with the water vapor. Even if the surface of the piezoelectric material is passivated with a non-metallic oxide, metal oxide, non-metallic nitride, or a metal nitride such as silicon oxide, aluminum oxide, silicon nitride, or aluminum nitride, the surface will still be populated with dipolar functional groups such as silanol or aluminum hydroxide which will significantly sorb water or other dipolar molecules. The adsorption of water vapor by the silanol groups on the quartz surface leads to corrosion issues and signal anomalies and difficulty in quantifying the response from the SAW and like device.

A number of different attempts have been made to eliminate the anomalous interference caused by the water vapor absorption. McGill et al. in *Surface and Interfacial Properties of Surface Acoustic Wave Gas Sensors*, supra, describe attempts to overcome the interference caused by adsorption of water vapor onto the quartz surface by plasma cleaning of the quartz surface followed by chemical modification of the quartz piezoelectric surface. The quartz surface was chemically modified by silanization of the surface with diphenyl tetramethyldisilazane, followed by coating the silanized surface with polyisobutylene, a polymer that selectively sorbs different chemical compounds. While this treatment partially overcomes the water vapor adsorption problem in that the silanized surface is superior to an unsilanized surface, the silanized surface still exhibits and anomalous results when exposed to water vapor. Because of this deleterious effect of water vapor on the SAW and like devices, the chemical sensors are not fully optimized.

Laser deposition of thin films is described by D. B. Chrisey and G. K. Hubler, Editors, in *Pulsed Laser Deposition of Thin Films* (Wiley, New York 1994), herein incorporated by reference.

SUMMARY AND OBJECTS OF THE INVENTION

An object of the present invention is to develop a chemical sensor that is relatively insensitive to water or water vapor.

Another object of the invention is to develop a sensor with a protective surface coating.

A further object of the invention is to provide a chemical sensor with a protective coating of diamond or DLC coating which reduces the sensitivity of the sensor to water and water vapor.

These and other objects of the invention have been obtained by coating a surface of a chemical sensor with a uniform protective coating to proviide a barrier to water and other molecules.

BRIEF DESCRIPTION OF THE DRAWINGS

FIGS. 5(a) and (b) are schematic illustration of front and end views of an optical total internal reflection chemical sensor device.

FIGS. 6(a) and (b) are schematic illustration of side and end views of a fiber optic chemical sensor device.

DETAILED DESCRIPTION OF THE INVENTION

Figure 1A:
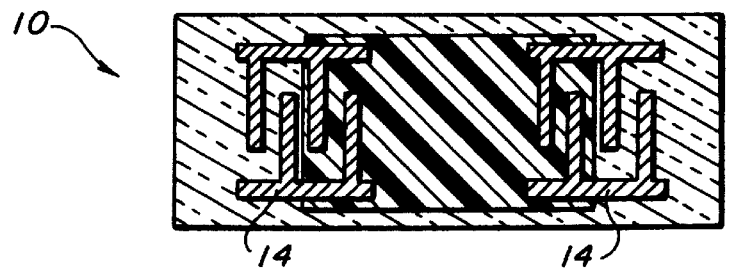
FIGS. 1(*a*) and (*b*) are schematic illustration of top and front views of a surface acoustic wave (SAW) device with its entire top surface coated with the protective coating.

The inventors discovered that if the substrate of a wave chemical sensor is coated with a protective coating of diamond or DLC coating, the anomalous results obtained when the device is exposed to dipolar molecules are reduced or eliminated.

The inventors also discovered that diamond or DLC can be coated uniformly on the substrate used in chemical sensor devices with sufficient bonding strength to prevent delamination during use.

The inventors also discovered that a chemoselective material can be coated on the protective coating with adequate adhesion between the chemoselective material and the protective coating during use. If a DLC coating is applied by the pulsed laser deposition method, as will be discussed below, a very uniform coating of carbon is provided with no pinholes in the DLC coating. The importance of this pinhole-free coating is that it protects the device in a corrosive environment by preventing the corrosive environment from contacting and corroding the quartz surface or the metal electrode(s) on the surface of the device. The term "pinhole-free" is used to indicate that no discontinuity in the diamond or DLC coating is present large enough to permit water molecules therethrough.

In general, the subject acoustic wave chemical sensor devices comprise a substrate that is responsive to an acoustical wave or optical signal, at least one transducer or electrodes in association with the substrate, a protective coating of diamond or DLC on the substrate, and a chemoselective or bioselective film on the protective coating.

The principle of operation of the acoustic wave device transducer involves the production of an acoustic wave that is generated on the surface or through the bulk of a substrate material and allowed to propagate. To generate the acoustic wave typically requires a piezoelectric material. Applying a time varying electric field to the piezoelectric material will cause a synchronous machanical deformation of the substrate with a coincident generation of an acoustic wave in the material. The time varying electric field is generated in the surface by the action of the time varying electrical field applied through one or more electrodes that are connected to the piezoelectric material via one or more matal wire bonds and to an electrical circuit. Another electrode or electrodes receives the wave at a distance from the first electrode or electrodes. The second electrode or electrodes is also connected via metal wire bonds to the electrical circuit and the piezoelectric material.

An optical waveguide chemical or biochemical sensor consists of a light source, an optical waveguide, a chemoselective film or coating, and a detedtor to analyze the light after interacting with the coating. The waveguide is utilized to propogate light to an active region of the device that contains the chemoselective coating. The light travels towards this coating and interacts with it. If analyte is present in the coating, the optical characteristics of the light may be altered and the change detected by some optically sensitive detector.

Figure 1B:
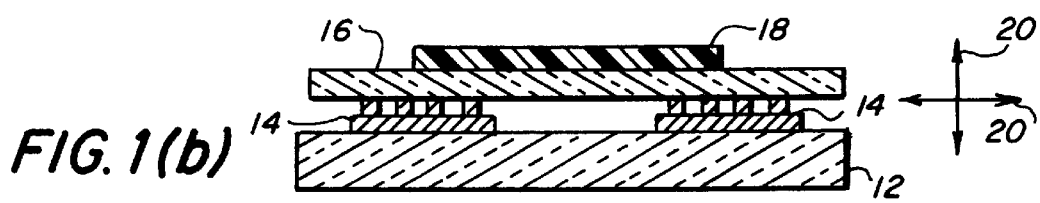

FIGS. 1(a) and (b) show a basic acoustic chemical sensor 10 that typically includes a piezoelectric substrate 12, transducers 14 disposed in a spaced relationship on the substrate, a protective coating of diamond or DLC 16 on device 10, and a chemoselective film 18 disposed on the protective coating. It should be understood that since deposition of diamond or DLC coating 16 is by PLD, the coating in reality is in contact with substrate 12 and around transducers 14. Arrows 20 indicate direction of surface particle displacement. The protective coating 16 need not cover or extend over the entire top surface of the device, as is shown in FIG. 1, but can cover only the active area of the device underneath the chemoselective coating, as illustrated in FIG. 4. Although FIG. 1 shows the transducers in the form of interdigitated fingers, the transducers can take other forms, as shown in FIG. 2, which illustrates another type of acoustic chemical sensor with similar structure as the SAW device illustrated in FIG. 1. Examples of acoustic chemical sensors that this invention pertains to include thickness-shear mode (TSM) or bulk acoustic wave (BAW), surface acoustic wave (SAW), flexural plate wave (FPW), and acoustic plate mode (APW) chemical sensor devices. Optical chemical or biochemical sensors include fiber optic waveguides and planar waveguides.

Figure 2A:
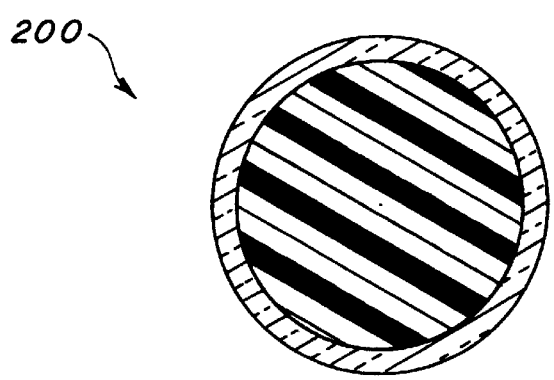
FIGS. 2(a) and (b) are schematic illustration of top and front views of a bulk acoustic wave (BAW) device having the protective coating on its top surface.
Figure 2B:
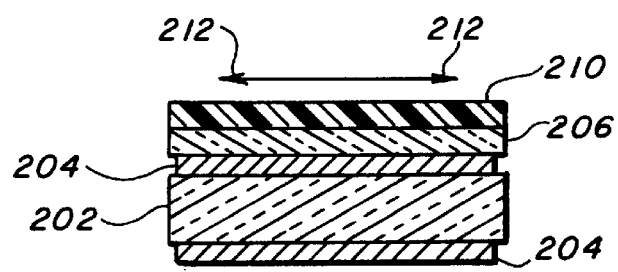

FIGS. 2(a) and (b) is an illustration of a thickness shear mode (TSM) acoustic device 200 which includes substrate 202 in the form of a disc, disc electrodes 204 diposed on opposing sides of and in contact with the substrate which function to propagate a wave through the device, protective coating 206 disposed in the top surface of the device, and a chemoselective film 210 disposed on the protective coating.

Figure 3A:
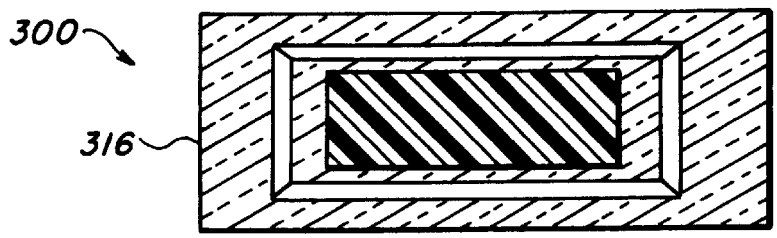
FIGS. 3(a) and (b) are schematic illustration of top and front views of a flexural plate wave (FPW) acoustic device having the protective coating on its top surface.
Figure 3B:
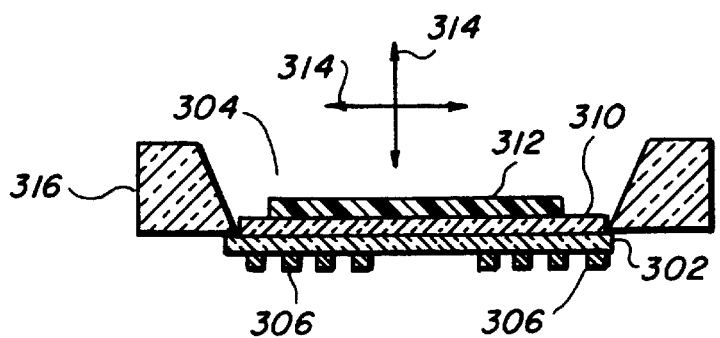

FIGS. 3(a) and (b) is an illustration of a flexural plate wave (FPW) acoustic device 300 which includes a rectangular substrate 302 with a central rectangular cavity 304, transducers 306 in the form of interdigitating fingers disposed on the underside of the device below the cavity 304, protective coating 310 disposed on the top surface and in the cavity of the device, and chemoselective coating 312 disposed on the upside of the device in the cavity 304 on the protective coating. Arrows 314 indicate direction of surface particle displacement. Silicon structure 316 surrounds the rectangular device, as shown in the top or elevation view.

Figure 4A:
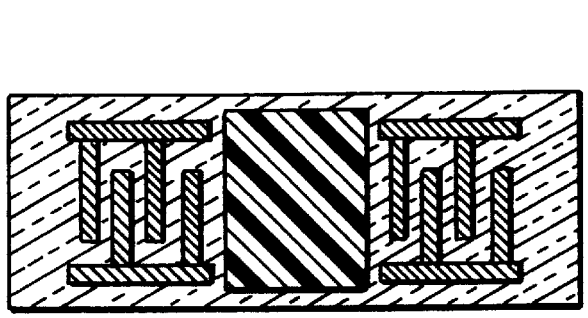
FIGS. 4(a) and (b) are schematic illustration of top and front views of a SAW device with a partial protective coating thereon in the area between the transducers.
Figure 4B:
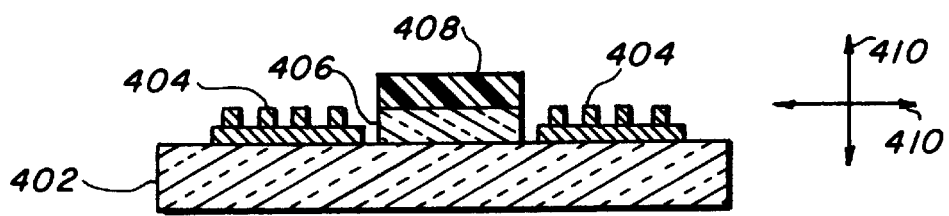

FIGS. 4(a) and (b) illustrate a partially coated SAW device 400 with substrate 402, transducers 404 disposed in spaced relationship on the substrate, protective coating 406 disposed on the substrate between the transducers, and a chemoselective coating 408 disposed on the protective coating between the transducers. The protective coating and the chemoselective film are coextensive, although they need not be. Arrows 410 indicate direction of surface particle displacement.

An optical chemical or biochemical sensor, commonly referred to as an optrode, includes a light source such as a semiconductor laser, light-emitting diode, or a halogen lamp; an optical waveguide such as a fiber optic or a planar waveguide substrate; a chemoselective or bioselective film deposited on the active area of the optrode exposed to an analyte; and a detector to monitor the optical characteristics of the optrode. Sorption of analyte to the chemoselective or bioselective coating modifies the optical characteristics of the optrode and this is detected as a change in refractive index or light intensity at one or more wavelengths of light.

Fiber optic waveguides for sensor applications are commonly manufactured from silica glass or quartz as the core of the fiber. Surrounding this core is a cladding material which exhibits a lower refractive index than the cladding to achieve internal reflectance. The chemoselective coating is typically applied at the distal tip of the fiber optic or along the side of the fiber optic where a portion of the cladding material has been removed.

Planar waveguide optical sensors utilize a planar substrate device as a light guide. The use of a planar waveguide normally invokes the use of evanescent wave techniques to take advantage of the large active surface area. Many of the published examples of these sensors utilize the fluorescent properties of a chemoselective or a bioselective coating and hence, the term Total Internal Reflection Fluorescence (TIRF) sensors.

Optical sensors that take advantage of the optical evanescent wave in their detection mechanism are sensitive to analyte sorbates at the interface between the active area of the sensor and the surrounding medium. For a chemoselective or a bioselective coated sensor, it is possible for analyte to distribute itself at the interface between the coating and the optical waveguide substrate. The interfacial sorption of an analyte between the coating and the optical waveguide substrate is undesirable because it can lead to slow sensor kinetic responses and significant responses from analyte that the chemoselective coating does not sorb strongly. An example of this is a quartz waveguide coated with a nonpolar chemoselective coating designed to detect hydrocarbon analytes. On exposure to humid air, the water molecules will concentrate at the polar interface between the chemoselective coating and the optical waveguide substrate. The effect of the interfacially sorbed water can affect the optical properties of the evanescent wave and result in undesirable sensor signal responses.

For optical bio-sensor applications that require immobilization of material to the sensor surface, a controlled partial oxidation of the DLC surface can be achieved by the use of an air or oxygen plasma. Hydroxyl groups suitable for immobilizing silane reagents and then a chemoselective coating can be generated by exposing the oxidized protective coating surface to water vapor.

FIGS. 5(a) and (b) illustrate an optical planar chemical sensor 500 that includes substrate or core 502, a protective coating of diamond or a DLC 504 disposed on the substrate, a chemoselective coating 506 disposed on the protective coating 504, and a light source 508 which directs light 510 into the substrate 502 through which the light is propagated.

FIGS. 6(a) and (b) illustrate a fiber optic chemical sensor device 600 which includes cylindrical substrate or core 602, cladding 604 surrounding the substrate, protective coating 606 disposed at the distal end of the device, and chemoselective film 608 disposed on the protective coating. The optical wave from light source 610 is directed into the core and propagates a light 612 through the core and through the protective coating and the chemoselective film and is directed into a detector as it exits the chemoselective film.

Thickness of the protective coating of diamond or a DLC on an acoustic or an optical chemical sensor device can be varied from 1 to 1000 nanometers (nm), preferably 10 to 350 nm, and even more preferably from 15 to 300 nm. Thickness should be effective to reduce anomalous interference caused by absorption of the water molecules at the interface of the protective coating and the substrate. If the protective coating is too thin, it will not be effective in reducing or completely eliminating the anomalous results, and if it is too thick, it will cause cracking and/or delamination.

Before application of the protective coating to a chemical sensor device described herein, the device is cleaned. The cleaning procedure typically involves rinsing the device in an organic solvent and then subjecting it to plasma cleaning, as is well known. Optionally, the surfce of the device can be silanized with a material such as diphenyltetramethyldisilazane (DPTMS) by immersing the cleaned device in liquid DPTMS, placing the immersed device into a partially evacuated chamber while heating the device to about 170° C. for about 12 hours. The silanized device is then removed and solvent cleaned with toluene, methanol, and chloroform, before applying the protective coating.

The chemical sensor device of the present invention is coated with a protective coating of diamond or DLC by placing the device to be coated in a high vacuum chamber. The chamber is evacuated to about $6 \times 10^{-7}$ torr or less at room temperature. A graphite target is then exposed to a pulsed laser, usually a Kr-F excimer laser with a wavelength of 248 nm, power density of 2 $J/cm^2$, a repetition rate of 5 Hz and a power level of about 200 mJ/pulse, which evaporates carbon from the surface of the graphite and deposits a diamond or DLC coating on the sensor device. Preferably, the device is rotated during the coating process and is located about 4 centimeters from the graphite target.

Other suitable laser sources for depositing the protective coating include argon fluorine at 193 nm, xenon fluorine at 308 nm and neodimium-yttrium aluminum garnet (Nb-YAG) at 1.05 micrometers.

To prepare the vacuum chamber for deposition of the protective coating on the device, the vacuum chamber is purged with an inert gas, such as argon. Diamond or a DLC film of an effective thickness is then applied. However, it has been discovered that by using the laser deposition technique, a much thinner coating of only about 50 angstroms is substantially pinhole-free with the result that the surface of the device is corrosion resistant.

Although a pulsed laser deposition technique can used to deposit a DLC coating onto the chemical sensing device, other techniques for depositing a diamond or a DLC coatig can be used, including ion beam deposition, ion beam assisted deposition, plasma deposition, sputtering, pulsed electron beam and chemical vapor deposition. However, when using other deposition techniques, care must be used not to damage or remove the metal electrodes on the surfaces, for instance, by etching or sputtering associated with the other processes, or damaging the quartz.

When depositing the protective coating on an acoustic wave chemical sensor device, usually diamond or a DLC is coated onto the device to adjust its operating frequency between 0.01 and 2% of the initial operating frequency, allowing the device to function correctly. The thickness of the coating can be controlled by removing the device and testing it, by using sensors or by monitoring the device signal during the deposition process to determine thickness of the protective coating.

Once the acoustic or optical chemical sensor device is coated with a protective coating, a chemoselective film is applied to the coating as a dilute solution in a solvent by an airbrush or a spin coating process. The thickness of the chemoselective film preferably does not exceed that which would reduce the frequency of a chemical sensor operating at 250 megahertz by about 250 kilohertz and is typically 0.5 nm to 10 microns, and more typically 1 nm to 300 nm.

An example of a chemoselective film is a polymeric material which is chosen so as to selectively sorb certain classes of chemical species. Chemoselective films or coatings used with chemical sensors have been described by R.

A. McGill et. al in *CHEMTECH,* 1994, Vol. 24 No. 9 pp. 27–37, and G. Harsanyi, in *Polymer Films In Sensor Applications* (Technomic, Lancaster, Pa. 1995), herein incorporated by reference. Preferred chemoselective films for aliphatic and aromatic hydrocarbons are polyalkenes, polyalkyl siloxanes, polyaryl siloxanes, polyalkylaryl siloxanes and porous carbons. Suitable chemoselective films for hydrogen bond basic analytes are zeolites, fluoropolyol and other fluorinated polyols. Suitable chemoselective films for hydrogen bond acidic analytes are polyethylene imines, polyanilines, polythiophenes, polyimides and polypyrroles. Broad spectrum sorptive films are polyepichlorohydrin and alkyl celluloses.

The finished device is incorporated into a detector system, as is well known in the art. The diamond or a DLC interface with the substrate is substantially insensitive to dipolar molecules with no anomalous results being observed when the device is exposed to an atmosphere of dipolar molecules such as water, alcohols, amines and the like. The device of the present invention is operable in a frequency range of 2 kilohertz to 10 gigahertz, preferably 0.2 megahertz to 2 gigahertz, and more preferably 1 to 500 megahertz. The area of sensing or the active area in such a device is on the order of 4 $cm^2$ or less. Active area is the area under the chemoselective film, where the chemoselective film covers the transducer.

Another approach to applying a chemoselective coating onto the protective coating of the device is through covalent attachment of a functionalized monolayer to the surface of the protective coating. This is carried out by partial oxidation of the protective coating by an air or oxygen plasma oxidation of the coating followed by treatment with a humid air stream and by reaction with alkoxy or halogenated organo silanes. Alternatively, the oxidized protective coating can be coated with gold and allowed to react with sulfur containing compounds.

The acoustic or optical chemical sensor device can be used as a biosensor in an aqueous environment since the substrate surface and the electrodes or the transducers are protected by diamond or a DLC coating. The diamond or a DLC coating surface can be functionalized by air or oxygen plasma oxidation of the surface followed by treatment with a humid air stream and by silanization or metallization by gold deposition. The gold can then be derivatized by organo thiol tether groups. The organo thiol reacted gold or the silanized surface can be used to attach a bioselective coating such as one member of an antibody-antigen, enzyme-substrate, sugar-lecithin or biotin-avidin pair.

As already noted, deposition of a thin layer of diamond or DLC coating on the surface of a SAW or a related device provides a dense, non-polar, an non-porous coating. The device so coated sorbs very little water. A 200 MHz SAW resonator device was coated with about 20–30 nm of DLC, which corresponded to an absolute frequency shift of about +1300 KHz. The DLC-coated device was tested at 298K with a series of water vapor exposures, each lasting 1000 seconds during the vapor exposure at the concentrations of 50 $mg/m^3$, 99 $mg/m^3$, 334 $mg/m^3$, 792 $mg/m^3$, 1548 $mg/m^3$, 3097 $mg/m^3$, 6107 $mg/m^3$, and 12,388 $mg/m^3$. Over this concentration range, there was no apparent SAW device signal response to the water vapor, indicationg minimal water sorption to the surface of the device. In contrast to this experiment, a SAW device passivated with about 30 nm thick coating of silica and tested under the same conditions, produced absolute frequency shift signals ranging from about +50 Hz at the lowest water vapor concentration to −800 Hz for the highest water vapor concentration.

In another such experiment, a polymeric coating of polyisobutylene was deposited on top of the DLC coated device, the polymeric coating thickness being about 20–30 nm, and tested as in the preceding paragraph with a range of water vapor concentrations. No apparent SAW signal response was observed to the water vapor exposures. In contrast, a SAW device passivated with a 30 nm thick coating of silica and similarly coated with polyisobutylene and tested under the same conditions, prodiced absolute frequency shift signals ranging from about +500 Hz at the lowest water vapor concentration to −800 Hz for the highest water vapor concentration.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A wave chemical sensor device comprising a substrate; a wave producing means associated with said substrate; a protective coating of diamond or a diamond-like carbon covering said substrate, said coating is of an effective thickness to reduce anomalous interference caused by dipolar molecules; and a chemoselective film on said protective coating.

2. The device of claim 1, wherein said coating has a thickness of about 1 to 1000 nanometers.

3. The device of claim 1, wherein said coating has a thickness of about 10 to 350 nanometers.

4. The device of claim 1, wherein said coating has a thickness of about 15 to 300 nanometers.

5. The device of claim 1, wherein said wave producing means is a pair of transducers disposed in spaced relationship on said substrate, wherein said substrate is piezoelectric and wherein said device is selected from the group consisting of surface acoustic wave, plate acoustic wave, and bulk acoustic wave devices.

6. The device of claim 1, which is an optical chemical sensor device.

7. The device of claim 1, wherein said substrate is quartz.

8. The device of claim 1, which operates at a frequency of 2 kilohertz to 25 gigahertz.

9. The acoustic wave chemical sensor of claim 1, wherein the thickness of the coating changes the frequency of the acoustic wave chemical sensor depending on the amount of applied coating.

10. The device of claim 1, wherein said chemoselective film is selected from the group consisting of polyalkenes, polyalkyl siloxanes, polyaryl siloxanes, polyalkylaryl siloxanes, porous carbons, fluoropolyol, fluorinated polyols, zeolites, polyethyleneimines, polyanilines, polythiophenes, polyimides, polypyrroles, polyepichlorohydrin, alkyl celluloses and mixtures thereof.

11. The device of claim 1, wherein said chemoselective film is selected from the group consisting of organo silanes; sulfur containing compounds; and silanes or sulfur containing tethers to one member of an antibody-antigen, enzyme-substrate, biotin-avidin sugar-lecithin pair.

* * * * *